(12) United States Patent
Nitta et al.

(10) Patent No.: US 10,371,632 B2
(45) Date of Patent: Aug. 6, 2019

(54) DATA CORRECTION METHOD IN FINE PARTICLE MEASURING DEVICE AND FINE PARTICLE MEASURING DEVICE

(71) Applicant: Sony Corporation, Tokyo (JP)

(72) Inventors: Nao Nitta, Tokyo (JP); Shingo Imanishi, Kanagawa (JP); Taichi Takeuchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 1025 days.

(21) Appl. No.: 14/404,196

(22) PCT Filed: Apr. 3, 2013

(86) PCT No.: PCT/JP2013/060164
§ 371 (c)(1),
(2) Date: Nov. 26, 2014

(87) PCT Pub. No.: WO2013/183345
PCT Pub. Date: Dec. 12, 2013

(65) Prior Publication Data
US 2015/0112627 A1 Apr. 23, 2015

(30) Foreign Application Priority Data
Jun. 6, 2012 (JP) ................. 2012-129080

(51) Int. Cl.
*G01B 21/00* (2006.01)
*G01N 15/10* (2006.01)
(Continued)

(52) U.S. Cl.
CPC ............. *G01N 21/64* (2013.01); *G01B 21/00* (2013.01); *G01N 15/1429* (2013.01);
(Continued)

(58) Field of Classification Search
CPC .............................. G01N 21/00; G01N 21/64
(Continued)

(56) References Cited

U.S. PATENT DOCUMENTS

| 4,643,566 A | 2/1987 | Ohe et al. |
| 5,258,791 A * | 11/1993 | Penney ................. A61B 3/103 |
| | | 351/208 |

(Continued)

FOREIGN PATENT DOCUMENTS

| CN | 101939633 A | 1/2011 |
| JP | 61-029738 | 2/1986 |

(Continued)

OTHER PUBLICATIONS

Chinese Office Action (with English translation) dated Aug. 18, 2016 in corresponding Chinese application No. 2013800285014 (15 pages).

(Continued)

*Primary Examiner* — Manuel A Rivera Vargas
(74) *Attorney, Agent, or Firm* — K&L Gates LLP

(57) ABSTRACT

To provide a technique capable of highly accurately measure the intensity and the spectrum of fluorescence and scattered light by effectively correcting measurement error that occurs due to variation of flow positions of fine particles in a channel. A data correction method for a fine particle measurement device is provided, which includes an intensity detection procedure capable of detecting light generated from a fine particle by emitting light onto the fine particle flowing through a channel, and obtaining intensity information about the light, a position detection procedure capable of obtaining position information about the fine particle, and a correction procedure for correcting the intensity information on the basis of the position information.

19 Claims, 10 Drawing Sheets

(51) Int. Cl.
  *G01N 15/14* (2006.01)
  *G01N 21/05* (2006.01)
  *G01N 21/21* (2006.01)
  *G01N 21/53* (2006.01)
  *G01N 21/64* (2006.01)

(52) U.S. Cl.
  CPC ......... *G01N 15/1459* (2013.01); *G01N 21/05* (2013.01); *G01N 21/21* (2013.01); *G01N 21/53* (2013.01); *G01N 21/645* (2013.01); *G01N 2015/1006* (2013.01); *G01N 2015/1415* (2013.01)

(58) Field of Classification Search
  USPC ................ 702/28, 30, 64, 85, 104; 250/225; 351/208
  See application file for complete search history.

(56) References Cited

U.S. PATENT DOCUMENTS

| | | | | |
|---|---|---|---|---|
| 5,436,464 | A * | 7/1995 | Hayano | G01N 21/94 250/225 |
| 6,465,781 | B1 * | 10/2002 | Nishimura | H01J 37/026 250/305 |
| 7,649,172 | B2 * | 1/2010 | Ozawa | G06T 5/006 250/306 |
| 2009/0323061 | A1 | 12/2009 | Novotny et al. | |
| 2010/0020321 | A1 | 1/2010 | Furuki et al. | |
| 2010/0314557 | A1 | 12/2010 | Hayashi et al. | |
| 2011/0315851 | A1 * | 12/2011 | Kishima | G02B 21/241 250/201.3 |
| 2012/0019824 | A1 * | 1/2012 | Dowaki | G01N 15/1434 356/337 |
| 2012/0050737 | A1 | 3/2012 | Dowaki et al. | |
| 2014/0226158 | A1 * | 8/2014 | Trainer | G02B 6/32 356/336 |

FOREIGN PATENT DOCUMENTS

| | | |
|---|---|---|
| JP | 02-304333 | 12/1990 |
| JP | 09-166541 | 6/1997 |
| JP | 2009-109197 | 5/2009 |
| JP | 2009-162650 | 7/2009 |
| JP | 2009-244080 | 10/2009 |
| JP | 2009-244080 A | 10/2009 |
| JP | 4489146 | 4/2010 |
| JP | 2011-149822 | 8/2011 |
| JP | 2012-047464 | 3/2012 |

OTHER PUBLICATIONS

International Search Report issued in connection with International Patent Application No. PCT/JP2013/060164, dated May 14, 2013. (2 pages).

Japanese Office Action dated Jan. 24, 2017 in corresponding Japanese application No. 2014-519863 (5 pages).

Japanese Office Action dated Jul. 17, 2018 in corresponding Japanese application No. 2017-172191 (3 pages).

* cited by examiner

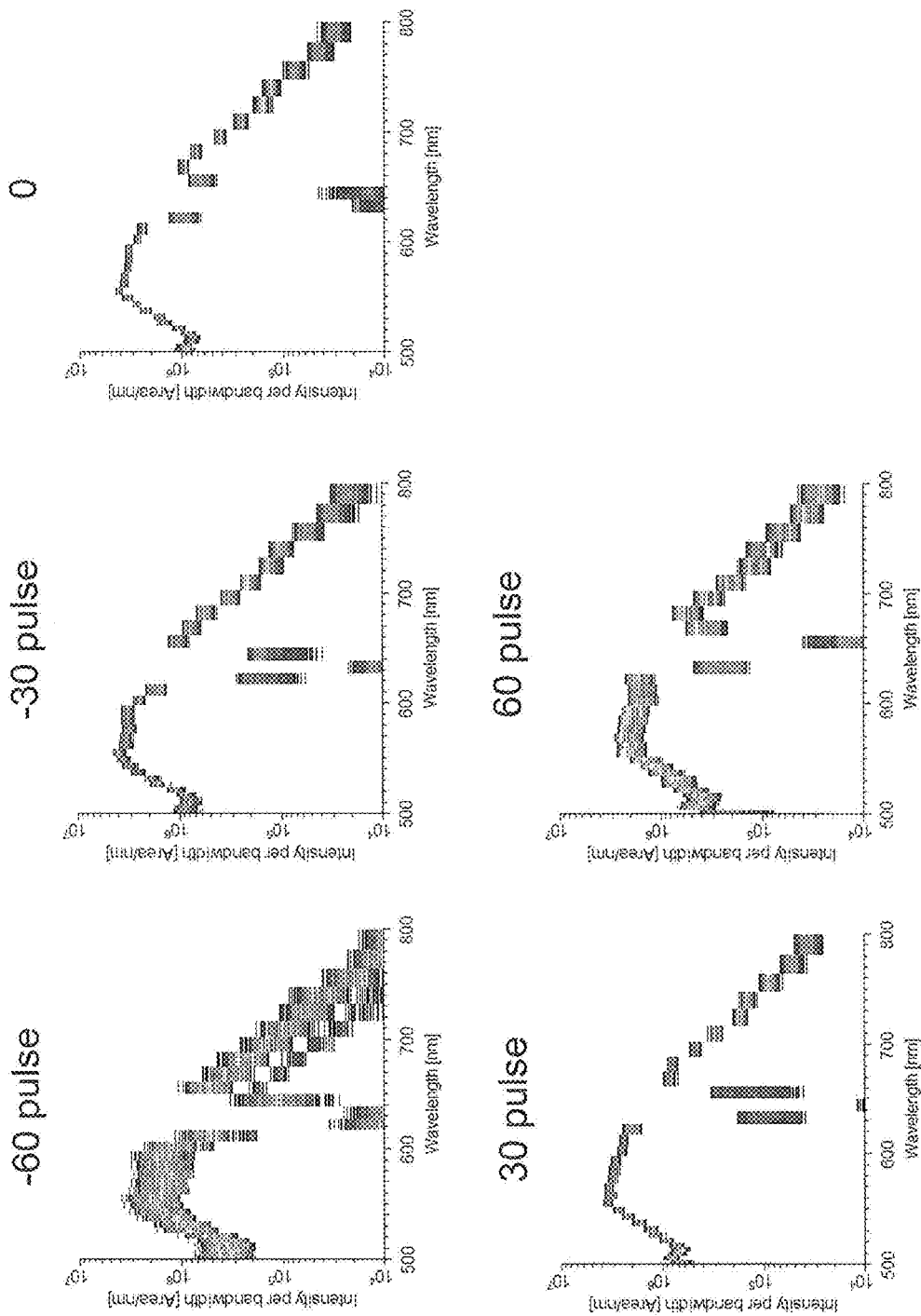

A

B

A

B

FIG. 8
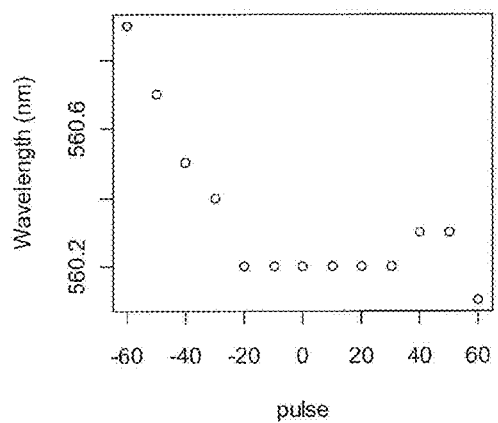
A
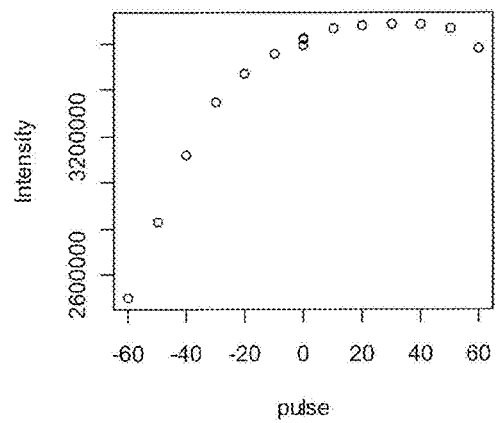
B
FIG. 9
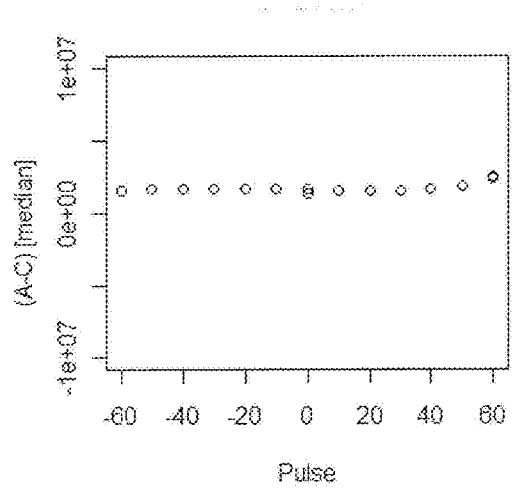
A
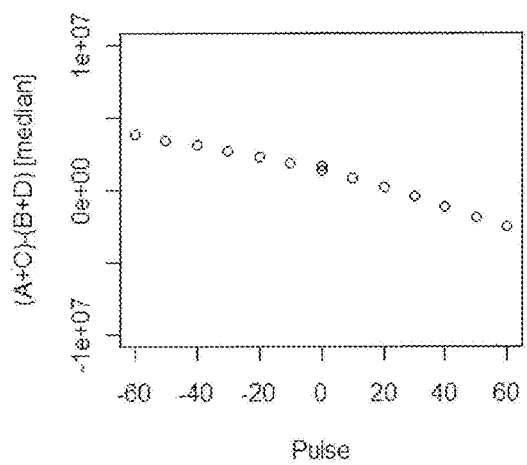
B

FIG. 10
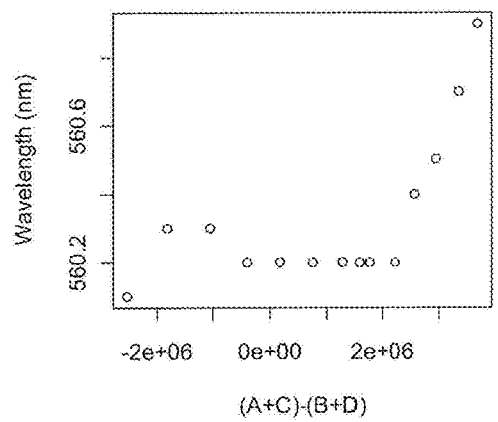
A
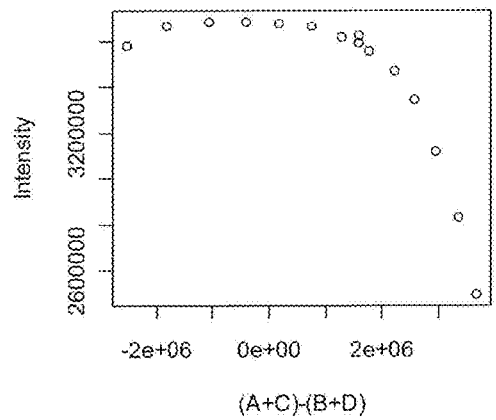
B
FIG. 11
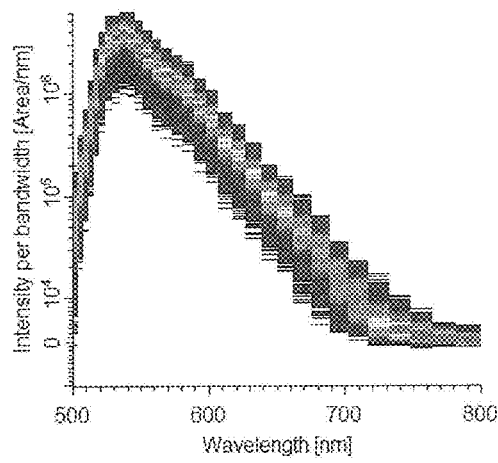
A
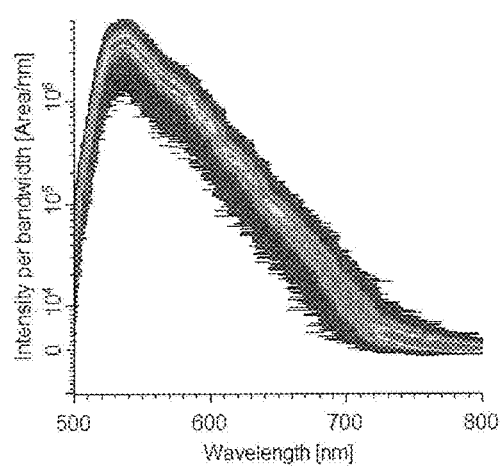
B

DATA CORRECTION METHOD IN FINE PARTICLE MEASURING DEVICE AND FINE PARTICLE MEASURING DEVICE

CROSS REFERENCES TO RELATED APPLICATIONS

The present application is a national stage of International Application No. PCT/JP2013/060164 filed on Apr. 3, 2013 and claims priority to Japanese Patent Application No. 2012-129080 filed on Jun. 6, 2012, the disclosure of which is incorporated herein by reference.

BACKGROUND

The present technique relates to a data correction method for a fine particle measurement device and a fine particle measurement device. More specifically, the present technique relates to, e.g., a data correction method for a fine particle measurement device for correcting measurement error caused by variation of flow positions of fine particles in a channel formed in a flow cell, a microchip, and the like.

A fine particle measurement device is known, which forms a laminar flow (which is also referred to as a sheath flow) including fine particles in a channel formed in a flow cell, a microchip, and the like, emits light onto the fine particles in the laminar flow, and detects fluorescence and scattered light generated from the fine particles. For example, a flow cytometer can measure and analyze the optical property of the fine particles such as cells and beads on the basis of the intensity or the spectrum of the fluorescence or the scattered light detected.

In the fine particle measurement device, the laminar flow is formed so that the fine particles flow substantially in the center of the channel, but the flow position of each fine particle in the channel varies, and therefore, measurement error caused by this variation is problematic. The variation of the flow position of the fine particles in the channel and the measurement error caused by this variation are especially large when the flow rate of the sample liquid laminar flow including the fine particles in the laminar flow is configured to be more than the flow rate of the sheath fluid laminar flow in order to reduce the time it takes to perform the measurement.

When the flow position in the channel varies among the fine particles, the relationship in the positions in terms of optics between the fine particles and the light emission system for the fine particles and the detection system of the fluorescence and the scattered light generated from the fine particles is different among the fine particles. As a result, measurement error caused by the deviation of the optical position occurs in the intensity and the spectrum of the fluorescence and the scattered light detected in each fine particle.

Patent Document 1 and Patent Document 2 disclose a technique for suppressing the measurement error caused by variation of the flow position of the fine particles. In the fluid particle analysis device described in Patent Document 1, detection light (scattered light) retrieved via an optical divider from forward scattered light, side scattered light or backward scattered light is detected by a quadrant photodiode, an area CCD, and the like. Then, the deviation of the positions between the center of the excitation light and the center of the sheath flow is detected from the detection position, and the position of the flow cell is adjusted so that this deviation of the positions stays within a predetermined range. Patent Document 2 describes a technique for detecting position information about fine particles by using polarization angle change that occurs in the scattered light generated from fine particles and adjusting the focal position of the excitation light or the position of the flow cell.

CITATION LIST

Patent Document

Patent Document 1: JP 9-166541 A
Patent Document 2: JP 2011-149822 A

SUMMARY

Problems to be Solved by the Invention

The measurement error due to the variation of the flow position of the fine particles is problematic when the fluorescence generated from the fine particles is measured as the spectrum. The fluorescence generated from the fine particles is divided into the spectrum using a spectral device such as a prism and a grating mirror. Then, the spectrum of the fluorescence is detected by a light reception device array having PMTs, photodiodes, and the like arranged in a one-dimensional manner and a two-dimensional light reception device such as a CCD and a CMOS. At this occasion, when the flow position of the fine particles vary, the wavelength range of the fluorescence incident upon one of the multiple independent detection channels arranged in the light reception device array or the two-dimensional light reception device may be different among the fine particles.

More specifically, when the wavelength range of the fluorescence projected from a fine particle k upon a detection channel n is $\lambda_k$ to $\lambda_{k+1}$ the wavelength range of the fluorescence projected from a fine particle 1, of which flow position in the channel is different from that of the fine particle k, is $\lambda_l$ to $\lambda_{l+1}$, and the values of $(\lambda_k, \lambda_{k+1})$ and $(\lambda_l, \lambda_{l+1})$ may be different. As a result, the fluorescent spectrum detected with each fine particle may involve measurement error caused by deviation of the wavelength range of the fluorescence incident upon the detection channel n.

It is a main object of the present technique to provide a technique capable of highly accurately measure the intensity and the spectrum of the fluorescence and the scattered light by effectively correcting the measurement error that occurs due to the variation of the flow positions of the fine particles in the channel.

Solutions to Problems

To solve the above problem, the present technique provides a data correction method for a fine particle measurement device, including: an intensity detection procedure capable of detecting light generated from a fine particle by emitting light onto the fine particle flowing through a channel, and obtaining intensity information about the light; a position detection procedure capable of obtaining position information about the fine particle; and a correction procedure for correcting the intensity information on the basis of the position information.

In the data correction method, in the position detection procedure, the position information about the fine particle in an X axis direction which is an emission direction of light onto the fine particle and/or the position information about the fine particle in a Z axis direction which is perpendicular to the X axis direction and a Y axis direction which is a flow direction of the fine particle may be obtained as the position information.

In the data correction method, in the position detection procedure, a detection device receives light of an S polarization component which is separated from scattered light generated from the fine particle and given astigmatism, and a light reception position of the S polarization component on the detection device may be obtained as the position information.

In the data correction method, in the position detection procedure, a detection device of which light reception surface is divided into multiple areas may be used as the detection device. More specifically, a detection device of which light reception surface is divided into four areas, which are an area A, an area B, an area C, and an area D, in a lattice manner is used as the detection device. The position information about the fine particle in the Z axis direction may be obtained from a difference $\Delta 1$ (A−C) of detection values in the area A and the area C which is not adjacent to the area A. Further, the position information about the fine particle in the X axis direction may be obtained from a difference $\Delta 2$ ((A+C)−(B+D)) between a summation (A+C) of detection values in the area A and the area C and a summation (B+D) of detection values in the area B and the area D.

In the data correction method, in the correction procedure, the intensity information may be corrected on the basis of the difference $\Delta 1$ and/or the difference $\Delta 2$. Alternatively, in the correction procedure, only the intensity information about the fine particle where the difference $\Delta 1$ and/or the difference $\Delta 2$ is within a predetermined range may be extracted.

When the light generated from the fine particle is detected by multiple different wavelength regions and the intensity information is obtained as spectrum information about the light in the intensity detection procedure of the data correction method, this spectrum information can be corrected on the basis of the position information in the correction procedure.

Further, the present technique provides a fine particle measurement device including: a light illumination unit configured to emit light onto a fine particle flowing through a channel; a light detection unit configured to detect light generated from the fine particle; a position detection unit configured to obtain position information about the fine particle; and an arithmetic computation unit configured to correct, on the basis of the position information, intensity information about light generated from the fine particle obtained by the light detection unit.

In the fine particle measurement device, the position detection unit may include: a first spectral device configured to separate scattered light generated from the fine particle into an S polarization component and a P polarization component; an S polarization detection device configured to receive light of the S polarization component; and an astigmatism device provided between the first spectral device and the S polarization detection device to give astigmatism to the S polarization component, and a light reception position of the S polarization component on the S polarization detection device is obtained as the position information. In the fine particle measurement device, the S polarization detection device, the light reception surface may be divided into multiple areas, and may be divided into four areas, which are an area A, an area B, an area C, and an area D, in a lattice manner.

In the fine particle measurement device, the arithmetic computation unit may correct the intensity information on the basis of: a difference $\Delta 1$ (A−C) of detection values in the area A and the area C which is not adjacent to the area A, and/or a difference $\Delta 2$ ((A+C)−(B+D)) between a summation (A+C) of detection values in the area A and the area C and a summation (B+D) of detection values in the area B and the area D. Alternatively, the arithmetic computation unit may extract only the intensity information about the fine particle where a difference $\Delta 1$ (A−C) of detection values in the area A and the area C which is not adjacent to the area A and/or a difference $\Delta 2$ ((A+C)−(B+D)) between a summation (A+C) of detection values in the area A and the area C and a summation (B+D) of detection values in the area B and the area D is within a predetermined range.

The fine particle measurement device may further include a second spectral device configured to separate the light generated from the fine particle into the scattered light and fluorescence, and the light detection unit may include a P polarization detection device configured to detect the P polarization component and a fluorescence detection device configured to detect the fluorescence.

Further, the fine particle measurement device may include, in the light detection unit, a third spectral device configured to separate the fluorescent, and the fluorescence detection device may be arranged with a plurality of independent light reception devices configured to detect the fluorescence separated by the third spectral device.

In the present technique, the "intensity information" includes information about a wavelength region of fluorescence detected by any given fine particle and the intensity of fluorescence in the wavelength region. More specifically, the "intensity information" includes information about the wavelength region of the fluorescence incident upon the light reception device and the intensity of the fluorescence in the wavelength region in a case where the florescence generated from any given fine particle is guided to and detected by the light reception device. Therefore, more specifically, "correction of the intensity information" means correction of, with regard to any given fine particle, the wavelength region of the fluorescence incident upon the light reception device and/or the intensity of the fluorescence in the wavelength region, on the basis of the position information about the fine particle.

In the present technique, the "fine particle" is considered to widely include bio-related fine particles such as cells, microorganisms, and liposome, or composite particles such as latex particles, gel particles, industrial particles.

The bio-related fine particles include, e.g., chromosome, liposome, mitochondria, organelle constituting various kinds of cells. The cells include animal cells (such as blood corpuscle cells) and plant cells. The microorganisms include bacteria such as colibacillus, virus such as tobacco mosaic virus, and bacteria such as yeast cells. Further, the bio-related fine particles include bio-related high polymer such as nucleic acid and protein, and compounds thereof. The industrial particles may be, for example, organic or inorganic high polymer materials and metals. The organic high polymer materials include polystyrene, styrene-divinylbenzene, and polymethyl methacrylate. The inorganic high polymer materials include glass, silica, and magnetic material. The metals include colloidal gold and aluminum. The shapes of these fine particles are generally spherical shapes in normal cases, but may be non-spherical shapes, and the size and the mass thereof are not particularly limited.

Effects of the Invention

The present technique provides a technique capable of highly accurately measuring the intensity and the spectrum of the fluorescence and the scattered light by effectively correcting the measurement error that occurs due to the variation of the flow positions of the fine particles in the channel.

Additional features and advantages are described herein, and will be apparent from the following Detailed Description and the figures.

BRIEF DESCRIPTION OF THE FIGURES

FIG. 5A is a graph illustrating an example of change of a fluorescent spectrum detected by the fluorescence detection device 32 in a case where the flow position of the fine particle P is moved in the Z axis direction.

FIGS. 8A and 8B are graphs illustrating an example of change of the peak wavelength (A) and the peak intensity (B) of the fluorescence 3 calculated on the basis of a detection result of the fluorescence detection device 32 in a case where the flow position of the fine particle P is moved in the X axis direction.

FIGS. 9A and 9B are graphs illustrating an example of change of the difference Δ1 and the difference Δ2 in a case where the flow position of the fine particle P is moved in the X axis direction.

FIGS. 10A and 10B are graphs illustrating an example of relationship between the peak wavelength (A) and the peak intensity (B) of the fluorescence 3 calculated on the basis of a detection result of the fluorescence detection device 32 and the difference Δ2 in a case where the flow position of the fine particle P is moved in the X axis direction.

FIGS. 11A and 11B are graphs illustrating an example of a fluorescent spectrum (A) before correction and a fluorescent spectrum (B) after correction.

MODE FOR CARRYING OUT THE INVENTION

A preferred embodiment for carrying out the present technique will be hereinafter explained with reference to drawings. The embodiment explained below shows an example of a typical embodiment of the present technique, and it is to be understood that the scope of the present technique should not be interpreted as being narrower because of the embodiment. The explanation will be made in the following order.

Figure 1:
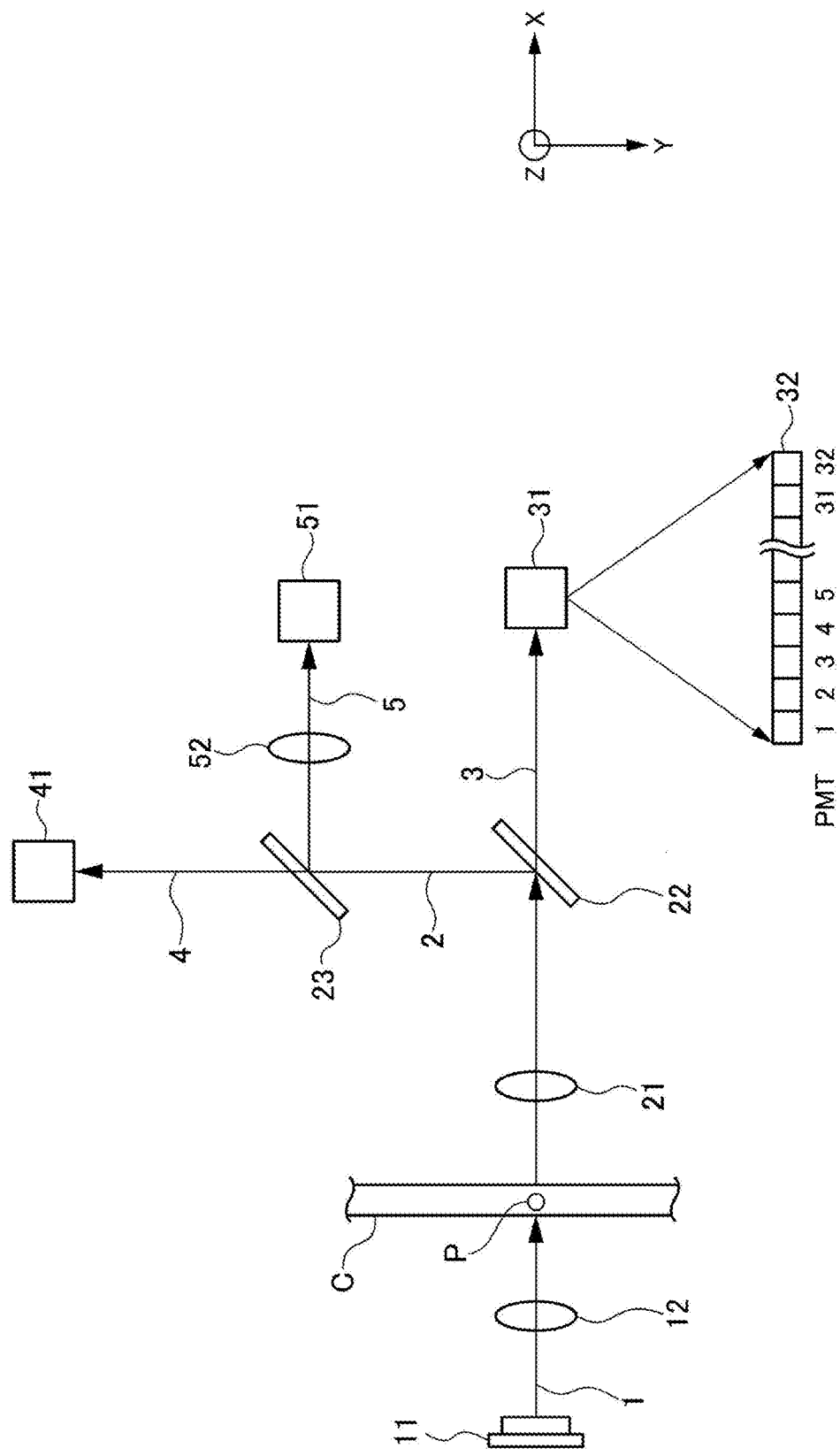
FIG. 1 is a figure for explaining a configuration of a measurement unit of a fine particle measurement device according to the present technique.

1. Configuration of fine particle measurement device
(1) Measurement unit
   (1-1) Light illumination unit
   (1-2) Light detection unit
   (1-3) Position detection unit
(2) Arithmetic computation unit
2. Data correction processing in fine particle measurement device
(1) Correction target
(2) Correction processing
3. Modification
(1) Light detection unit
(2) Position detection unit
4. Data correction method and data correction program
1. Configuration of Fine Particle Measurement Device
(1) Measurement Unit FIG. 1 is a figure for explaining a configuration of a measurement unit of a fine particle measurement device according to the present technique. The fine particle measurement device according to the present technique is roughly constituted by a measurement unit shown in the figure and an arithmetic computation unit not shown in the figure. The measurement unit includes a light illumination unit configured to emit excitation light 1 onto a fine particle P flowing through a channel C, a light detection unit configured to detect scattered light 2 and fluorescence 3 generated by the fine particle P, and a position detection unit configured to obtain position information about the fine particle P.

(1-1) Light Illumination Unit

The light illumination unit includes a light source 11 configured to emit the excitation light 1 and an object lens 12 configured to condense the excitation light 1 onto the fine particle P flowing through the channel C formed in a flow cell, a microchip and the like. Depending on the purpose of measurement, the light source 11 is selected, as necessary from a laser diode, an SHG (Second Harmonic Generation) laser, a solid state laser, a gas laser, a high-illuminance LED (Light Emitting Diode), and the like. As necessary, the light illumination unit may be provided with an optical device other than the light source 11 and the object lens 12.

(1-2) Light Detection Unit

The light detection unit includes a condensing lens 21, a spectral device 22, a spectral device 31, a fluorescence detection device 32, and a P polarization detection device 41.

The condensing lens 11 condenses the scattered light 2 and the fluorescence 3 generated from the fine particle P emitted from the excitation light 1. The scattered light 2 may be various kinds of scattered lights such as forward scattered light, side scattered light, Rayleigh scattering, and Mie scattering. The fluorescence 3 may be fluorescence generated from the fine particle P itself or fluorescence generated from a fluorescent material labeled on the fine particle P.

The spectral device 22 separates the scattered light 2 and the fluorescence 3 condensed by the condensing lens 11. The spectral device 22 is made of a dichroic mirror that reflects only the light of a particular wavelength and allows a wavelength component other than that to pass through, and in the fine particle measurement device according to the present embodiment, the spectral device 22 is made of one that reflects the scattered light 2 and allows the fluorescence 3 to pass through.

The spectral device 31 is a prism, a grating mirror, and the like, and further divides the fluorescence 3 divided by the spectral device 22 into the spectrum and projects it on the fluorescence detection device 32. The fluorescence detection device 32 detects the fluorescence 3 divided into the spectrum by the spectral device 22. The fluorescence detection device 32 is arranged with multiple independent light reception devices, and each light reception device detects the light of the fluorescence 3 in the wavelength region projected upon being divided by the spectral device 31 into the spectrum. In the fine particle measurement device according to the present embodiment, a PMT array having 32-channel PMTs (photo multiplier tubes) arranged in one-dimensional manner as the light reception devices is used as the fluorescence detection device 32. The fluorescence detection device 32 converts the intensity information about the detected fluorescence 3 into an electric signal, and outputs the intensity information to the arithmetic computation unit. It should be noted that, for example, a photodiode array and a two-dimensional light reception device such as a CCD and a CMOS may be used as the fluorescence detection device 32.

When the light reception device array or the two-dimensional light reception device is used for the fluorescence detection device 32 in combination with the spectral device 31, the fluorescence 3 generated from the fine particle P can be obtained as the spectrum (see FIG. 11 explained later).

The P polarization detection device 41 detects the P polarization component 4 included in the scattered light 2 separated by the spectral device 22. The P polarization detection device 41 may be made of, for example, a PD (Photo diode), a CCD (Charge Coupled Device), or a PMT (Photo-Multiplier Tube). The P polarization detection device 41 converts the intensity information about the detected P polarization component 4 into an electric signal, and outputs the intensity information to the arithmetic computation unit. The size, the internal structure, and the like about the fine particle P can be analyzed from the intensity information about the P polarization component 4.

(1-3) Position Detection Unit

The position detection unit includes a spectral device 23, an S polarization detection device 51, and an astigmatism device 52.

The spectral device 23 is configured to separate incident unpolarized light into two polarization of which oscillation directions are perpendicular to each other, and separates the scattered light 2 separated by the spectral device 22 into a P polarization component 4 and an S polarization component 5. More specifically, of the incident scattered light 2, the spectral device 23 allows the P polarization component 4 to pass through, and reflects the S polarization component 5.

Figure 2:
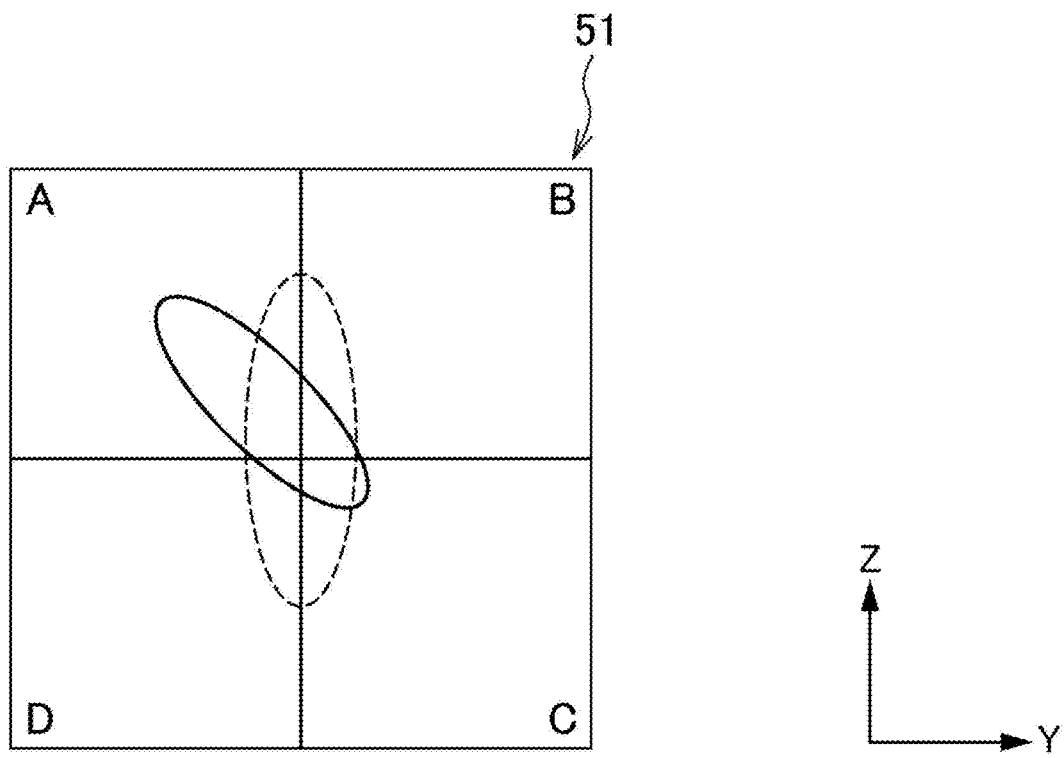
FIG. 2 is a figure for explaining a configuration of a light reception surface of an S polarization detection device 51.

The S polarization detection device 51 is to detect the S polarization component 5 separated by the spectral device 23, and the light reception surface thereof is divided into multiple areas. In the fine particle measurement device according to the present embodiment, as shown in FIG. 2, the S polarization detection device 51 is made of a quadrant photodiode of which light reception surface is divided into four areas, which are an area A, an area B, an area C, and an area D, in the lattice manner.

The astigmatism device 52 is a cylindrical lens arranged between the spectral device 23 and the S polarization detection device 51, and gives astigmatism to the S polarization component 5 transmitting toward the S polarization detection device 51. The position detection unit obtains, as the position information about the fine particle P, the light reception position (formed image pattern), on the light reception surface of the polarization detection device 51, of the S polarization component 5 having the astigmatism, and outputs the position information about the fine particle P to the arithmetic computation unit. The light reception position (formed image pattern) of the S polarization component 5 on the light reception surface of the polarization detection device 51 will be explained later in details.

(2) Arithmetic Computation Unit

The arithmetic computation unit performs processing to correct the intensity information about the fluorescence 3 and the P polarization component 4 which are input from the fluorescence detection device 32 and the P polarization detection device 41, respectively, of the light detection unit, on the basis of the position information of the fine particle P which is input from the position detection unit. The arithmetic computation unit is constituted by a hard disk, a CPU, a memory, and the like storing an OS and a program for executing this processing.

2. Data Correction Processing in Fine Particle Measurement Device

Subsequently, the correction processing performed by the arithmetic computation unit to correct the intensity information about the fluorescence 3 and the P polarization component 4 will be explained in details.

(1) Correction Target

Figure 3:
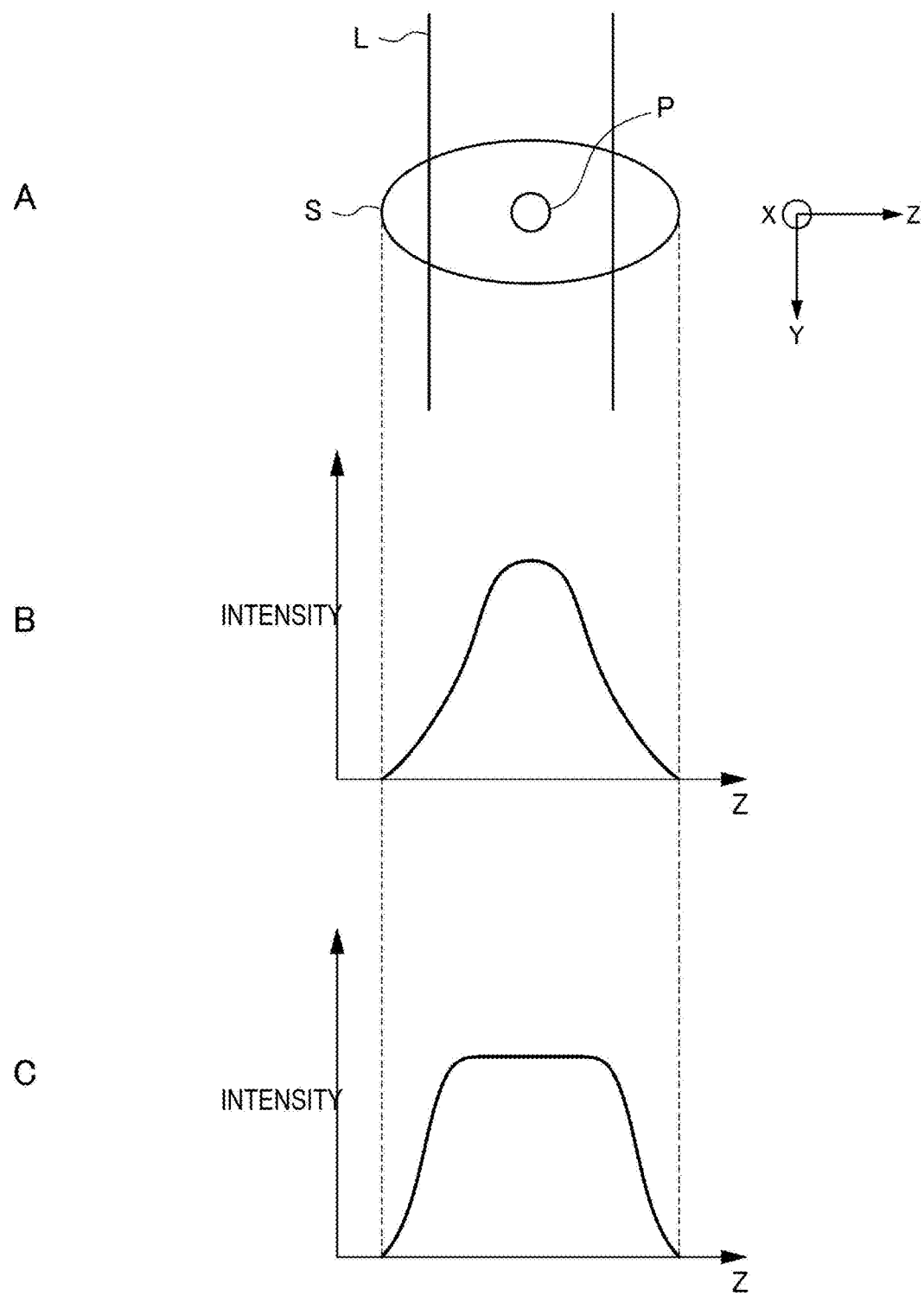
FIGS. 3A to 3C are figures for explaining a laminar flow L flowing through a channel C and a laser spot S of excitation light 1 emitted onto a fine particle P in the laminar flow L.

FIG. 3A illustrates the laminar flow L flowing through the channel C and the laser spot S of the excitation light 1 emitted onto the fine particle P in the laminar flow L. In the figure, the emission direction of the excitation light 1 emitted onto the fine particle P will be defined as X axis direction, the liquid feeding direction of the laminar flow L is defined as Y axis direction, and the direction perpendicular to the X axis direction and the Y axis direction is defined as Z axis direction.

The laminar flow L is formed so that the fine particle P flows substantially in the center of the channel C, but the flow position of the fine particle P varies in the Z axis direction. The intensity of the laser spot S is Gaussian distribution (B) or top flat distribution (C) as shown in FIGS. 3B, 3C, respectively, and the intensity of the laser spot S is the highest in the center and low in the periphery in the Z axis direction. In either case, when the fine particle P passes through the central position of the laser spot S, and the focal position of the excitation light 1 matches the flow position of the fine particle P, the emission intensity of the fine particle P by the excitation light 1 is the highest. On the other hand, when the fine particle P flows at a peripheral position away from the center of the laser spot S, and the focal position of the excitation light 1 does not match the flow position of the fine particle P, the emission intensity of the fine particle P by the excitation light 1 is lower. Therefore, the emission intensity of the excitation light 1 may be different among the fine particles P, and the intensities of the scattered light 2 and the fluorescence 3 generated from the fine particles P become different, which causes measurement error. However, top flat optical system of FIG. 3C is designed so that the emission intensity change caused by the deviation of the position decreases in the central part of the laminar flow L, and therefore, top flat optical system of FIG. 3C is less affected as compared with the Gaussian optical system of FIG. 3B. Similar measurement error may also occur due to variation of the flow position of the fine particle P in the X axis direction.

The deviation of the optical positions between the fine particle P and the light illumination unit due to the variation of the flow position of the fine particle P is also the factor that causes the wavelength range of the fluorescence 3 incident upon each of the PMT1 to 32 of the fluorescence detection device to be different among the fine particles P. More specifically, when the wavelength range of the fluorescence 3 projected from fine particle $P_k$ onto the detection channel k is $\lambda_k$ to $\lambda_{k+1}$ the wavelength range of the fluorescence 3 projected from the fine particle $P_l$ of which flow position in the channel C is different from that of the fine particle $P_k$ is $\lambda_l$ to $\lambda_{l+1}$, and therefore, the values of ($\lambda_k$, $\lambda_{k+1}$) and ($\lambda_l$, $\lambda_{l+1}$) may be different. As a result, the fluorescent spectrum detected with each fine particle P may involve measurement error caused by deviation of the wavelength range of the fluorescence 3 incident upon the detection channel k (see FIGS. 5A and 5B explained later).

(2) Correction Processing

The arithmetic computation unit performs processing to correct the measurement error, which is caused by the variation of the intensity of the fluorescence 3 caused by variation of the flow position of the fine particle P and the variation of the wavelength range of the fluorescence 3 incident upon each PMT of the fluorescence detection device 32, on the basis of the position information about the fine particle P.

First, the arithmetic computation unit derives the difference of the detection values between multiple areas provided on the light reception surface of the S polarization detection device 51. More specifically, the arithmetic computation unit derives the difference Δ1 (A−C) and the difference Δ2 ((A+C)−(B+D)) for the detection values in the area A, the area B, the area C, and the area D of the quadrant photodiode as shown in FIG. 2.

When the fine particle P passes the central position of the laser spot S of FIG. 3A, and the focal position of the excitation light 1 matches the flow position of the fine particle P, the formed image pattern (light reception position), on the light reception surface of the S polarization detection device 51, of the S polarization component 5 having the astigmatism given by the astigmatism device 52 is an image indicated by a dotted line in FIG. 2. On the other hand, when the fine particle P flows through the peripheral position away from the center of the laser spot S, and the focal position of the excitation light 1 does not match the flow position of the fine particle P, the formed image pattern is an image indicated by a solid line in FIG. 2. More specifically, the formed image pattern of the S polarization component 5 changes according to the flow position of the fine particle P, and the ratio of the S polarization component 5 projected onto the area A to the area D increases in accordance with the flow position of the fine particle P. Therefore, the pattern of the detection value of the S polarization component 5 in the area A to the area D directly reflects the flow position of the fine particle P.

The inventors of the present application have found that the position information about the fine particle P in the Z axis direction of FIG. 3A can be obtained from the difference Δ1 (A−C), and the position information about the fine particle P in the X axis direction of FIG. 3A can be obtained from the difference Δ2 ((A+C)−(B+D)).

When the flow cell formed in the channel C in which the fine particles P flow is moved by a stepping motor in the Z axis direction, the shape of the fluorescent spectrum changes as follows: the intensity of the fluorescence 3 of the fine particle P decreases due to the deviation of the optical position in accordance with the increase of the amount of movement as shown in FIG. 5A, and therefore, the shape of the fluorescent spectrum is more greatly dispersed, and the shape of the fluorescent spectrum changes. In the figure, the horizontal axis denotes a wavelength, and the vertical axis denotes an intensity (fluorescent intensity per wavelength), and the color scale indicates the frequency. A number above each graph is the number of pulses which indicates the amount of movement of the stepping motor.

Figure 4:
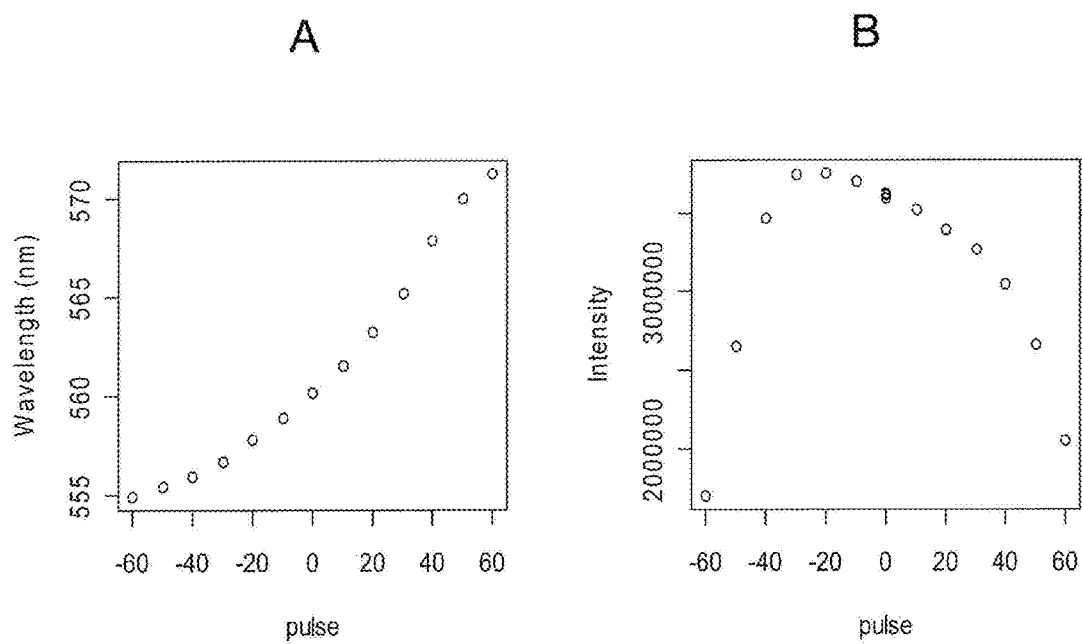
FIGS. 4A and 4B are graphs illustrating an example of change of a peak wavelength (A) and a peak intensity (B) of fluorescence 3 calculated on the basis of a detection result of a fluorescence detection device 32 in a case where the flow position of the fine particle P is moved in a Z axis direction.
Figure 5B:
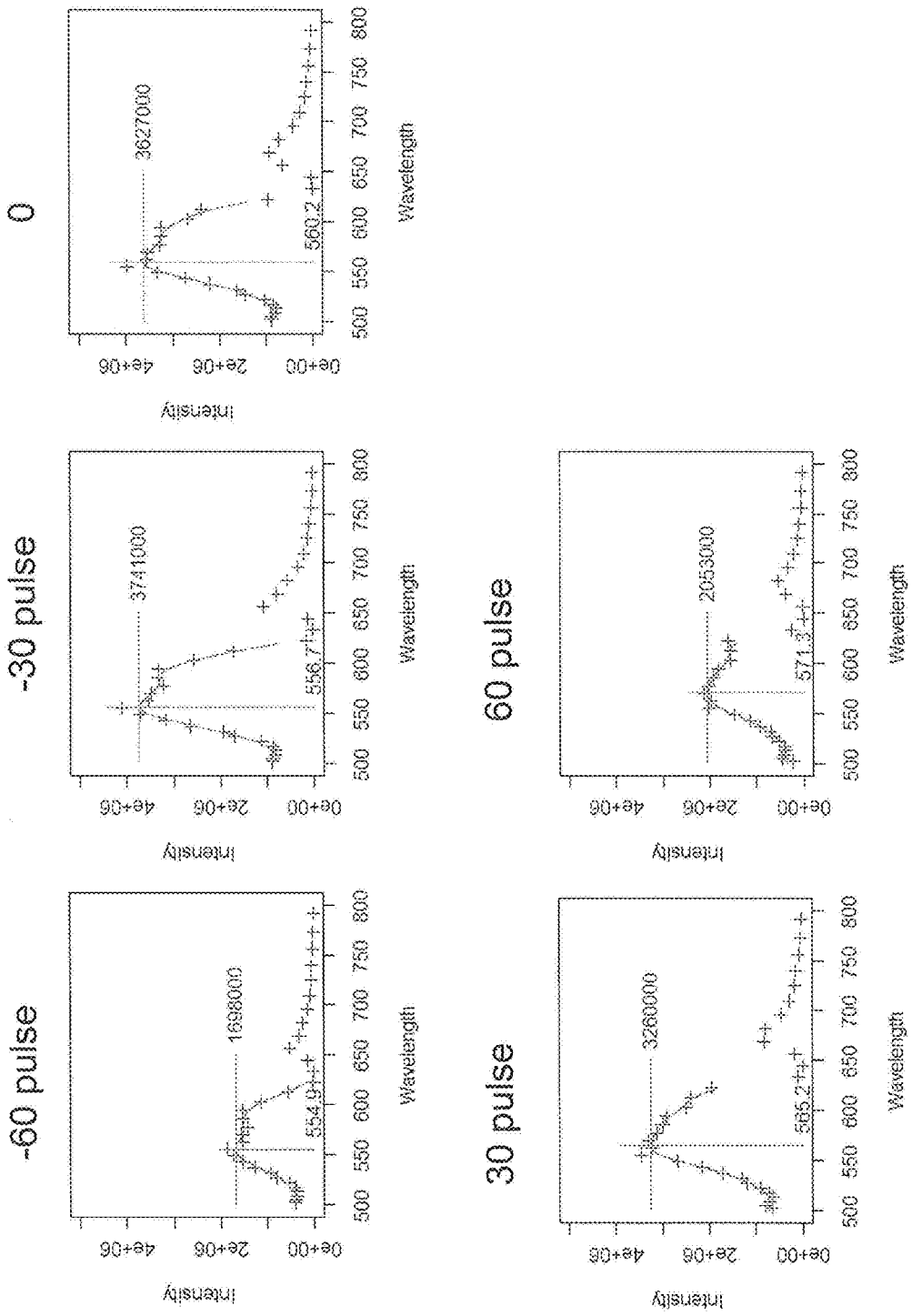
FIG. 5B is a graph illustrating an example of an average value (average spectrum) of a fluorescent spectrum detected by the fluorescence detection device 32 in a case where the flow position of the fine particle P is moved in the Z axis direction.

In order to quantify the change of the fluorescent spectrum, the average spectrum of the fluorescent spectrum measured as shown in FIG. 5B is calculated, and smoothing process is done according to Kernel smoothing method, whereby the maximum value of the curved line of the result and the wavelength at the maximum value are obtained. The above is done for each amount of movement of the stepping motor, and FIG. 4A is obtained by plotting the relationship between the amount of movement of the pulse and the fluorescent peak wavelength, and FIG. 4B is obtained by plotting the relationship between the amount of movement of the pulse and the fluorescent peak intensity. In any of the graphs, the horizontal axis denotes the amount of movement of the pulse, and the vertical axis denotes the fluorescent peak wavelength in FIG. 4A, and denotes the fluorescent intensity in FIG. 4B. The result in this case indicates that, when the position of the fine particle P in the Z axis direction is deviated, the peak wavelength and the intensity of the detected fluorescent spectrum are changed.

Figure 6:
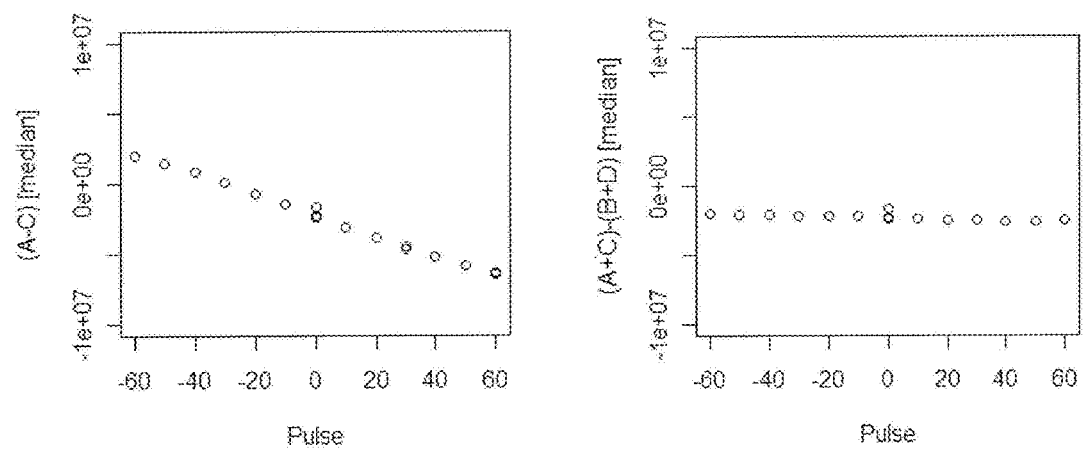
FIGS. 6A and 6B are graphs illustrating an example of change of a difference Δ1 and a difference Δ2 in a case where the flow position of the fine particle P is moved in the Z axis direction.
Figure 7:
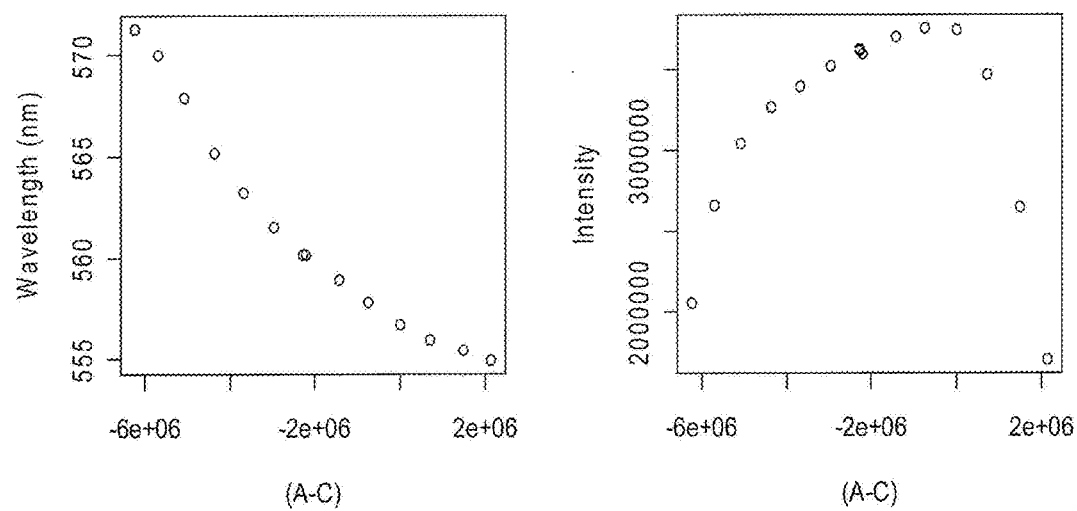
FIGS. 7A and 7B are graphs illustrating an example of relationship between the peak wavelength (A) and peak intensity (B) of the fluorescence 3 calculated on the basis of a detection result of the fluorescence detection device 32 and the difference Δ1 in a case where the flow position of the fine particle P is moved in the Z axis direction.

FIGS. 6A and 6B show the change of the difference Δ1 (A−C) and the difference Δ2 ((A+C)−(B+D)) when the flow cell through which the fine particles P flow is moved by the stepping motor in the Z axis direction. As shown in the figure, only the difference Δ1 changes in correlation with the amount of movement. Therefore, it is understood that the position information about the fine particle P in the Z axis direction can be obtained from the difference Δ1 (A−C). Further, the relationship between the difference Δ1 (A−C) and the peak wavelength and peak intensity of the detected fluorescent spectrum can be obtained by combining the result of FIGS. 6A and 6B and the result of FIGS. 4A and 4B (FIGS. 7A and 7B). Therefore, by using the difference Δ1 (A−C) as the position information about the fine particle P in the Z axis direction, the distortion of the wavelength and intensity of the fluorescence 3 incident upon the PMT that is caused by the deviation of the position in the Z axis direction can be corrected.

In a case where the flow cell through which the fine particles P flow is moved by the stepping motor in the X axis direction, the analysis is also performed in the same manner as the movement in the Z axis direction explained above. FIG. 8 is a result obtained by analyzing the fluorescent spectrum according to the same method as FIGS. 4A and 4B when the flow cell is moved in the X axis direction. FIG. 8A illustrates the relationship between the amount of movement and the fluorescent peak wavelength when the flow cell is moved by the stepping motor in the X axis direction, and FIG. 8B illustrates the relationship between the amount of movement and the fluorescent peak intensity. The horizontal axis of FIG. 8 denotes the number of pulses which indicates the amount of movement of the stepping motor. The figure indicates that the change in the fluorescent peak wavelength is smaller but the fluorescent peak intensity changes more greatly when the flow cell is moved in the X direction than when it is moved in the Z axis direction.

FIGS. 9A and 9B show the change of the difference Δ1 (A−C) and difference Δ2 ((A+C)−(B+D)) when the flow cell through which the fine particles P flow is moved by the stepping motor in the X axis direction. As shown in the figure, only the difference Δ2 changes in correlation with the amount of movement. Therefore, it is understood that the position information about the fine particle Pin the X axis direction can be obtained from the difference Δ2 ((A+C)−(B+D)). Further, the relationship between the difference Δ2 ((A+C)−(B+D)) and the peak wavelength and the peak intensity of the detected fluorescent spectrum can be obtained by combining the result of FIGS. 9A and 9B and the result of FIGS. 8A and 8B (FIGS. 10A and 10B). Therefore, by using Δ2 ((A+C)−(B+D)) as the position information about the fine particle P in the X axis direction, the distortion of the wavelength and intensity of the fluorescence incident upon the PMT that is caused by the deviation of the position in the X axis direction can be corrected.

Subsequently, the arithmetic computation unit uses the difference Δ1 (A−C) and the difference Δ2 ((A+C)−(B+D)) as the position information about the fine particle P to perform the correction processing for correcting the intensity information about the fluorescence 3 and the P polarization component 4. The correction processing is performed by generating a regression curved line from the relationship shown in FIGS. 7A and 7B and FIGS. 10A and 10B, and correcting the intensity information in accordance with the values of the differences Δ1 and Δ2 by using the calibration expression representing the regression curved line.

More specifically, for all of the fine particles P, the intensity information about the fluorescence 3 as well as the differences Δ1 and Δ2 are obtained as the position information. Then, for each of the fine particles P, the amount of distortion of the fluorescent wavelength and the fluorescent intensity caused by the deviation of the flow position of the fine particle P is calculated from the values of differences Δ1 and Δ2 using the calibration expression, and accordingly, the amount of distortion is corrected.

The fluorescent wavelength is corrected by calculating the amount of distortion (the amount of change) of the wavelength range of the fluorescence 3 incident upon each PMT of the fluorescence detection device 32 from the values of the differences Δ1 and Δ2, and shifting the detection wavelength range of each PMT by the amount of distortion thus calculated. The fluorescent intensity is corrected by calculating the distortion rate (change rate) of the intensity value of the fluorescence 3 incident upon each PMT from the values of the differences Δ1 and Δ2, and dividing the intensity value of each PMT by the distortion rate thus calculated. In this case, the correction of the intensity information about the fluorescence 3 has been explained, but the intensity information about the P polarization component 4 can be corrected in the same manner.

FIGS. 11A and 11B illustrate an example of fluorescent spectrum before and after the correction. FIG. 11A illustrates a spectrum chart before the correction. In FIG. 11A, the horizontal axis denotes a wavelength, and the vertical axis denotes the fluorescent intensity, and the color scale denotes the frequency. FIG. 11B shows a result obtained by correcting, on this data, the effect of the deviation of the wavelength caused by the deviation of the position using the difference Δ1. For example, suppose that the 10-th detection channel (PMT 10) of the fluorescence detection device 32 is designed to detect the fluorescence in wavelength 540.0 nm to 546.0 nm. In this case, the value of the difference Δ1 of any given fine particle P indicates that the detection wavelength range of the 10-th detection channel is considered to be deviated by a wavelength of 1.5 nm. In the correction in this case, for the fine particle P, the measurement result of the 10-th detection channel is adopted as the measurement result in the wavelength region 541.5 nm to 547.5 nm. In FIG. 11A which is before the correction, the spectrum is such that the dispersion is large because of the measurement error caused by the variation of the flow position of the fine particle P, and the spectrum is in the distorted shape. In FIG. 11B which is after the correction, the spectrum is such that the dispersion is small, and the spectrum is a smooth shape.

The regression curved line and the calibration expression are preferably obtained using the micro beads for calibration, before the measurement of the fine particle P used as the sample. The regression curved line and the calibration expression may also be obtained as follows in a more simplified manner.

More specifically, first, while the position of the flow cell is fixed, the intensity information about the fluorescence 3 as well as the differences Δ1 and Δ2 serving as the position information are obtained for the micro beads for calibration. Then, two or more beads or two or more beads populations of which differences Δ1 and Δ2 are different are extracted. Two beads populations of which differences Δ1 and Δ2 are different may be, for example, beads populations surrounded by Gate 1 and Gate 2. For example, FIG. 12 shows beads populations surrounded by Gate 1 and Gate 2.

Subsequently, the feature amount of fluorescent spectrum is calculated for the extracted beads or the populations thereof, and the regression curved line and the calibration expression which associates the values of the differences Δ1 and Δ2 and the feature amount with each other are obtained. The feature amount may be the peak wavelength, the peak intensity, and the like of the fluorescence incident upon each PMT of the fluorescence detection device 32.

Figure 12:
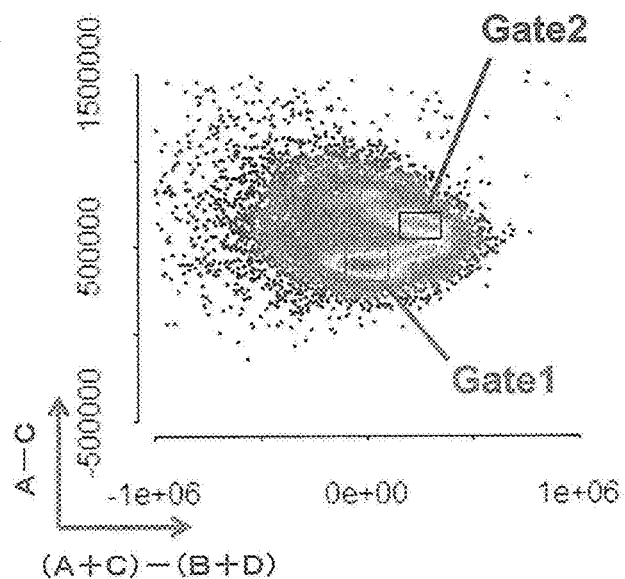
FIG. 12 is an example of a distribution diagram plotting a population of fine particles P where the difference Δ1 and the difference Δ2 are adopted as the axes.

Further, a method for eliminating the measurement error caused by the deviation of the position of the fine particle P without using the regression curved line and the calibration expression explained above includes a method for extracting only the intensity information about the fine particle P of which difference Δ1 and/or the difference Δ2 is within a predetermined range such as Gate 1 and Gate 2 shown in FIG. 12, and adopting it as a measurement result.

As described above, according to the fine particle measurement device according to the present technique, the position information about each of the fine particles P is obtained, and the intensity information about the scattered light 2 and the fluorescence 3 of the fine particle P is corrected, so that the measurement error caused by the deviation of the position of the fine particle P can be compensated, and the intensity and spectrum of the scattered light 2 and the fluorescence 3 can be measured accurately. According to the fine particle measurement device according to the present technique, the fluorescent spectrum dispersed less greatly and having smooth shape can be obtained, and therefore, the fluorescent spectrum of the fine particle P serving as the sample can be recognized in a more intuitive manner, and data comparison can be done easily for comparison with the fluorescent spectrum obtained using the fluorescent spectrophotometer and the like.

3. Modification (1) Light Detection Unit

Figure 13:
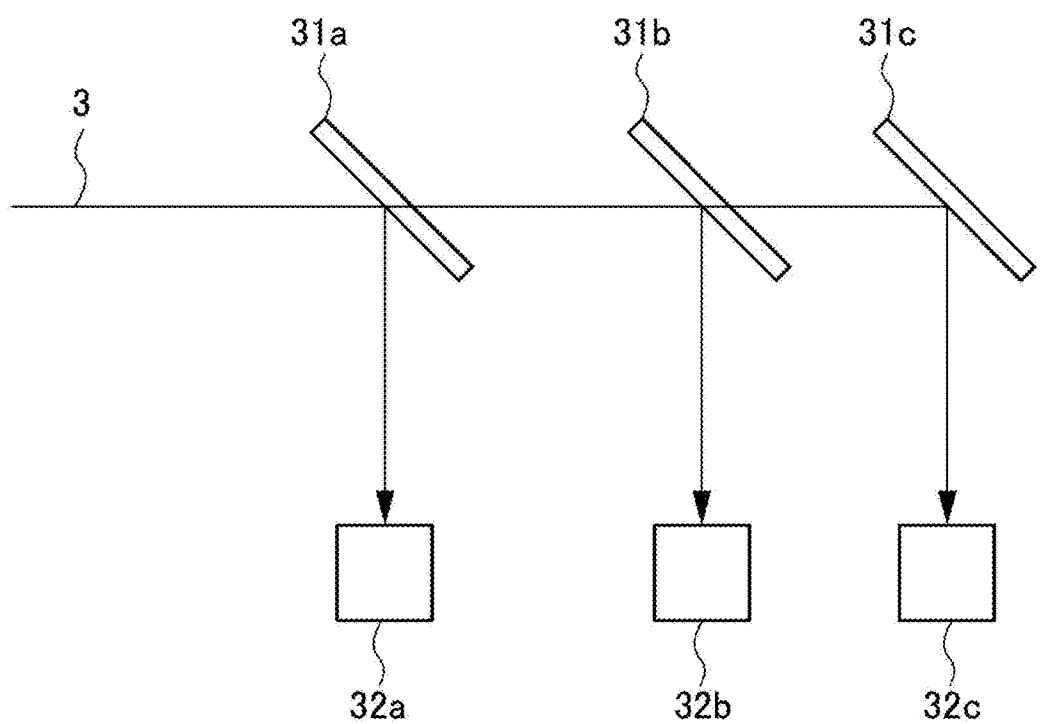
FIG. 13 is a figure for explaining a configuration of a modification of a light detection unit.

The fine particle measurement device according to the above embodiment has been explained in which, for example, the light detection unit is constituted by combining the spectral device 31 and the fluorescence detection device 32 which is the light reception device array or the two-dimensional light reception device, and the fluorescence 3 generated from the fine particle P is obtained as the spectrum. In the fine particle measurement device according to the present technique, as shown in FIG. 13, the light detection unit may use multiple wavelength selection devices (three wavelength selection devices having reference numerals 31a, 31b, 31c in this case) to select only a desired wavelength region from the fluorescence 3, and fluorescence detection devices (three fluorescence detection devices having reference numerals 32a, 32b, 32c in this case) perform detection. The wavelength selection devices 31a, 31b, 31c may be made of dichroic mirrors and the like that reflect the light in the particular wavelength region and allow the light other than that to pass through. The fluorescence detection devices 32a, 32b, 32c may be made of a PD (Photo diode), a CCD (Charge Coupled Device), a PMT (Photo-Multiplier Tube), and the like. It should be noted that the configuration is not limited to the combination of the three wavelength selection devices and the three fluorescence detection devices explained here. Alternatively, a single or two or more wavelength selection devices and a single or two or more fluorescence detection devices may be provided.

(2) Position Detection Unit

In the explanation about the fine particle measurement device according to the above embodiment, for example, the quadrant photodiode is used as the position detection unit, and the formed image pattern (light reception position), on the light reception surface of the polarization detection device 51, of the S polarization component 5 having astigmatism is obtained as the position information about the fine particle P. Alternatively, in the fine particle measurement device according to the present technique, a high speed camera may be used as a position detection unit, and the high speed camera directly takes a picture of a fine particle P flowing through the channel C, and the position information about the fine particle P may be obtained through image processing.

4. Data Correction Method and Data Correction Program

A data correction method according to the present technique corresponds to correction processing executed by the arithmetic computation unit of the fine particle measurement device explained above. The arithmetic computation unit of the fine particle measurement device stores a data correction program for executing this data correction.

The program is stored and held in a hard disk, and is read to a memory under the control of the CPU and the OS, and the above correction processing is executed. The program may be a program recorded in a computer-readable recording medium. The recording medium is not particularly limited as long as it is a computer-readable recording medium, but more specifically, for example, disk-shaped recording media such as a flexible disk and a CD-ROM are used. Alternatively, a tape-type recording medium such as a magnetic tape may be used.

The data correction method according to the fine particle measurement device according to the present technique may be configured as follows.

(1) A data correction method for a fine particle measurement device, including:

an intensity detection procedure capable of detecting light generated from a fine particle by emitting light onto the fine particle flowing through a channel, and obtaining intensity information about the light;

a position detection procedure capable of obtaining position information about the fine particle; and a correction procedure for correcting the intensity information on the basis of the position information.

(2) The data correction method according to (1), wherein in the position detection procedure, the position information about the fine particle in an X axis direction which is an emission direction of light onto the fine particle and/or the position information about the fine particle in a Z axis direction which is perpendicular to the X axis direction and a Y axis direction which is a flow direction of the fine particle are obtained as the position information.

(3) The data correction method according to (1) or (2), wherein in the position detection procedure, a detection device receives light of an S polarization component which is separated from scattered light generated from the fine particle and given astigmatism, and a light reception position of the S polarization component on the detection device is obtained as the position information.

(4) The data correction method according to (3), wherein in the position detection procedure, a detection device of which light reception surface is divided into multiple areas is used as the detection device.

(5) The data correction method according to (4), wherein a detection device of which light reception surface is divided into four areas, which are an area A, an area B, an area C, and an area D, in a lattice manner is used as the detection device, and the position information about the fine particle in the Z axis direction is obtained from a difference $\Delta 1$ (A−C) of detection values in the area A and the area C which is not adjacent to the area A.

(6) The data correction method according to (5), wherein in the position detection procedure, the position information about the fine particle in the X axis direction is obtained from a difference $\Delta 2$ ((A+C)−(B+D)) between a summation (A+C) of detection values in the area A and the area C and a summation (B+D) of detection values in the area B and the area D.

(7) The data correction method according to (6), wherein in the correction procedure, the intensity information is corrected on the basis of the difference $\Delta 1$ and/or the difference $\Delta 2$.

(8) The data correction method according to (6), wherein in the correction procedure, only the intensity information about the fine particle where the difference $\Delta 1$ and/or the difference $\Delta 2$ is within a predetermined range is extracted.

(9) The data correction method according to any of (4) to (7), wherein a quadrant photodiode is used as the detection device.

Further, the fine particle measurement device according to the present technique may be configured as follows.

(1) A fine particle measurement device including:

a light illumination unit configured to emit light onto a fine particle flowing through a channel;

a light detection unit configured to detect light generated from the fine particle;

a position detection unit configured to obtain position information about the fine particle; and an arithmetic computation unit configured to correct, on the basis of the position information, intensity information about light generated from the fine particle obtained by the light detection unit.

(2) The fine particle measurement device according to (1), wherein the position detection unit includes:

a first spectral device configured to separate scattered light generated from the fine particle into an S polarization component and a P polarization component;

an S polarization detection device configured to receive light of the S polarization component; and an astigmatism device provided between the first spectral device and the S polarization detection device to give astigmatism to the S polarization component, and a light reception position of the S polarization component on the S polarization detection device is obtained as the position information.

(3) The fine particle measurement device according to (2), wherein a light reception surface of the S polarization detection device is divided into a plurality of areas.

(4) The fine particle measurement device according to (3), wherein the light reception surface of the S polarization detection device is divided into four areas, which are an area A, an area B, an area C, and an area D, in a lattice manner (5) The fine particle measurement device according to (4), wherein the arithmetic computation unit corrects the intensity information on the basis of:

a difference $\Delta 1$ (A–C) of detection values in the area A and the area C which is not adjacent to the area A, and/or, a difference $\Delta 2$ ((A+C)–(B+D)) between a summation (A+C) of detection values in the area A and the area C and a summation (B+D) of detection values in the area B and the area D.

(6) The fine particle measurement device according to (4), wherein the arithmetic computation unit extracts only the intensity information about the fine particle where a difference $\Delta 1$ (A–C) of detection values in the area A and the area C which is not adjacent to the area A and/or a difference $\Delta 2$ ((A+C)–(B+D)) between a summation (A+C) of detection values in the area A and the area C and a summation (B+D) of detection values in the area B and the area D is within a predetermined range.

(7) The fine particle measurement device according to any of (3) to (6), wherein the S polarization detection device is a quadrant photodiode.

(8) The fine particle measurement device according to any of (2) to (7), wherein the astigmatism device is a cylindrical lens.

(9) The fine particle measurement device according to any of (2) to (7) further including a second spectral device configured to separate the light generated from the fine particle into the scattered light and fluorescence, and wherein the light detection unit includes a P polarization detection device configured to detect the P polarization component and a fluorescence detection device configured to detect the fluorescence.

(10) The fine particle measurement device according to any of (1) to (10), wherein the light detection unit includes a third spectral device configured to separate the fluorescent, and the fluorescence detection device is arranged with a plurality of independent light reception devices configured to detect the fluorescence separated by the third spectral device.

INDUSTRIAL APPLICABILITY

According to the present technique, the measurement error caused by variation of the flow position of the fine particle in the channel can be effectively corrected, and the intensity and spectrum of the fluorescence and the scattered light can be measured with a high degree of accuracy. Therefore, the present technique can be preferably applied to a fine particle measurement device for analyzing optical property of fine particles such as cells in more details, and more particularly, the present technique can be preferably applied to a spectrum-type flow cytometer.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

1 Excitation light
11 Light source
12 Object lens
2 Scattered light
21 Condensing lens
22 Spectral device
23 Spectral device
3 Fluorescence
31 Spectral device
31a, 31b, 31c Wavelength selection device
32, 32a, 32b, 32c Fluorescence detection device
4 P polarization component
41 P polarization detection device
5 S polarization component
51 S polarization detection device
52 Astigmatism device
C Channel
L Laminar flow
P Fine particle
S Laser spot

The invention claimed is:

1. A data correction method for a fine particle measurement device, comprising:

an intensity detection procedure capable of detecting light generated from a fine particle by emitting light onto the fine particle flowing through a channel, and obtaining intensity information about the light;

a position detection procedure capable of obtaining position information about the fine particle relative to a central position within the channel at a point when the fine particle passes through the emitted light by forming an image pattern divided into a plurality of light reception areas such that the image pattern changes according to a flow position of the fine particle within the channel at the point when the fine particle passes through the emitted light wherein the position information about the fine particle is obtained in a Z axis direction as the position information, and the Z axis direction is perpendicular to an X axis direction which is an emission direction of light onto the fine particle and a Y axis direction which is a flow direction of the fine particle; and a correction procedure for correcting the intensity information on the basis of the position information.

2. The data correction method according to claim 1, wherein in the position detection procedure, the position information about the fine particle is obtained in the X axis direction.

3. The data correction method according to claim 2, wherein in the position detection procedure, a detection device receives light of an S polarization component which is separated from scattered light generated from the fine particle and given astigmatism, and a light reception position of the S polarization component on the detection device is obtained as the position information.

4. The data correction method according to claim 3, wherein in the position detection procedure, a detection device of which light reception surface is divided into multiple areas is used as the detection device.

5. The data correction method according to claim 4, wherein a detection device of which light reception surface is divided into four areas, which are an area A, an area B, an area C, and an area D, in a lattice manner is used as the detection device, and the position information about the fine particle in the Z axis direction is obtained from a difference $\Delta 1$ (A−C) of detection values in the area A and the area C which is not adjacent to the area A.

6. The data correction method according to claim 5, wherein in the position detection procedure, the position information about the fine particle in the X axis direction is obtained from a difference $\Delta 2$ ((A+C)−(B+D)) between a summation (A+C) of detection values in the area A and the area C and a summation (B+D) of detection values in the area B and the area D.

7. The data correction method according to claim 6, wherein in the correction procedure, the intensity information is corrected on the basis of at least one of the difference $\Delta 1$ or the difference $\Delta 2$.

8. The data correction method according to claim 7, wherein a quadrant photodiode is used as the detection device.

9. The data correction method according to claim 6, wherein in the correction procedure, only the intensity information about the fine particle where at least one of the difference $\Delta 1$ or the difference $\Delta 2$ is within a predetermined range is extracted.

10. A fine particle measurement device comprising:
a light illumination unit configured to emit light onto a fine particle flowing through a channel;
a light detection unit configured to detect light generated from the fine particle;
a position detection unit configured to obtain position information about the fine particle relative to a central position within the channel at a point when the fine particle passes through the emitted light, by forming an image pattern divided into a plurality of light reception areas such that the image pattern changes according to a flow position of the fine particle within the channel at the point when the fine particle passes through the emitted light, wherein the position information about the fine particle is obtained in a Z axis direction as the position information, and the Z axis direction is perpendicular to an X axis direction which is an emission direction of light onto the fine particle and a Y axis direction which is a flow direction of the fine particle; and
an arithmetic computation unit configured to correct, on the basis of the position information, intensity information about light generated from the fine particle obtained by the light detection unit.

11. The fine particle measurement device according to claim 10, wherein the position detection unit includes:

a first spectral device configured to separate scattered light generated from the fine particle into an S polarization component and a P polarization component;
an S polarization detection device configured to receive light of the S polarization component; and
an astigmatism device provided between the first spectral device and the S polarization detection device to give astigmatism to the S polarization component, and
a light reception position of the S polarization component on the S polarization detection device is obtained as the position information.

12. The fine particle measurement device according to claim 11, wherein a light reception surface of the S polarization detection device is divided into a plurality of areas.

13. The fine particle measurement device according to claim 12, wherein the light reception surface of the S polarization detection device is divided into four areas, which are an area A, an area B, an area C, and an area D, in a lattice manner.

14. The fine particle measurement device according to claim 13, wherein the arithmetic computation unit corrects the intensity information on the basis of at least one of:
a difference $\Delta 1$ (A−C) of detection values in the area A and the area C which is not adjacent to the area A, or
a difference $\Delta 2$ ((A+C)−(B+D)) between a summation (A+C) of detection values in the area A and the area C and a summation (B+D) of detection values in the area B and the area D.

15. The fine particle measurement device according to claim 14, wherein the S polarization detection device is a quadrant photodiode.

16. The fine particle measurement device according to claim 15, wherein the astigmatism device is a cylindrical lens.

17. The fine particle measurement device according to claim 16 further comprising a second spectral device configured to separate the light generated from the fine particle into the scattered light and fluorescence, and
wherein the light detection unit includes a P polarization detection device configured to detect the P polarization component and a fluorescence detection device configured to detect the fluorescence.

18. The fine particle measurement device according to claim 17, wherein the light detection unit includes a third spectral device configured to separate the fluorescent, and
the fluorescence detection device is arranged with a plurality of independent light reception devices configured to detect the fluorescence separated by the third spectral device.

19. The fine particle measurement device according to claim 13, wherein the arithmetic computation unit extracts only the intensity information about the fine particle where at least one of a difference $\Delta 1$ (A−C) of detection values in the area A and the area C which is not adjacent to the area A or a difference $\Delta 2$ ((A+C)−(B+D)) between a summation (A+C) of detection values in the area A and the area C and a summation (B+D) of detection values in the area B and the area D is within a predetermined range.

* * * * *